United States Patent
Sota et al.

(10) Patent No.: US 9,049,991 B2
(45) Date of Patent: Jun. 9, 2015

(54) METHOD OF DISCRIMINATING LONGITUDINAL MELANONYCHIA AND VISUALIZING MALIGNANCY THEREOF

(75) Inventors: Takayuki Sota, Tokyo (JP); Juzo Fujii, Yokohama (JP); Hiroshi Koga, Matsumoto (JP)

(73) Assignee: MITAKA KOHKO CO., LTD., Tokyo (JP)

( * ) Notice: Subject to any disclaimer, the term of this patent is extended or adjusted under 35 U.S.C. 154(b) by 67 days.

(21) Appl. No.: 13/518,589

(22) PCT Filed: Dec. 22, 2010

(86) PCT No.: PCT/JP2010/073090
§ 371 (c)(1),
(2), (4) Date: Jun. 22, 2012

(87) PCT Pub. No.: WO2011/078206
PCT Pub. Date: Jun. 30, 2011

(65) Prior Publication Data
US 2012/0268462 A1    Oct. 25, 2012

(30) Foreign Application Priority Data
Dec. 24, 2009    (JP) .................. 2009-292289

(51) Int. Cl.
*G09G 5/00*    (2006.01)
*A61B 5/00*    (2006.01)

(52) U.S. Cl.
CPC .............. *A61B 5/0077* (2013.01); *A61B 5/449* (2013.01)

(58) Field of Classification Search
None
See application file for complete search history.

(56) References Cited

U.S. PATENT DOCUMENTS

| | | | | |
|---|---|---|---|---|
| 2004/0109608 | A1* | 6/2004 | Love et al. | 382/224 |
| 2004/0267102 | A1* | 12/2004 | Skladnev et al. | 600/315 |
| 2012/0041275 | A1 | 2/2012 | Sota et al. | |

FOREIGN PATENT DOCUMENTS

| | | |
|---|---|---|
| JP | 2008-154761 | 7/2008 |
| JP | 2010-252895 | 11/2010 |
| JP | 2010-252904 | 11/2010 |

OTHER PUBLICATIONS

Ronger, Sandra, et al. "Dermoscopic examination of nail pigmentation." Archives of dermatology 138.10 (2002): 1327-1333.*
Hance, Gregory A., et al. "Unsupervised color image segmentation: with application to skin tumor borders." Engineering in Medicine and Biology Magazine, IEEE 15.1 (1996): 104-111.*
Pacheco, María del Carmen López, et al. "Implementation and analysis of relief patterns of the surface of benign and malignant lesions of the skin by microtopography." Physics in medicine and biology 50.23 (2005): 5535.*

(Continued)

*Primary Examiner* — Edward Martello
(74) *Attorney, Agent, or Firm* — Greenblum & Bernstein, P.L.C.

(57) ABSTRACT

In a digital color image of longitudinal melanonychia, RGB parameter values of each pixel are assumed as three components to form a three-dimensional vector. Latitudinal and longitudinal variables are obtained for each three-dimensional vector in an RGB space. The latitudinal and longitudinal variables are used to define a distribution of points, and from the distribution, a discrimination index is found. The discrimination index is classified according to a threshold, to discriminate whether the longitudinal melanonychia is malignant or benign. The distribution of points is displayed to realize visualization of the malignancy of the longitudinal melanonychia.

2 Claims, 5 Drawing Sheets

(56) References Cited

OTHER PUBLICATIONS

Douglas. "RMS and RSS in Error Analysis." The Math Forum (2007).*

Iyatomi et al.; "An Internet-based Melanoma Screening System with Acral Volar Lesion Support;" 30th Annual International IEEE EMBS Conference, Vancouver, British Columbia, Canada, Aug. 20-24, 2008.*

Nakatochi et al., "Development of an Algorithm to Extract Specific Waveform Image Pattern for Diagnosis of Nail Apparatus Melanoma", The Society of Chemical Engineers, Japan, 2007, pp. 570-580.

Search report from International Application No. PCT/JP2010/073090, mail date is Feb. 8, 2011.

International Preliminary Report on Patentability and Written Opinion for International Application No. PCT/JP2010/073090, mail date is Aug. 23, 2012.

* cited by examiner

METHOD OF DISCRIMINATING LONGITUDINAL MELANONYCHIA AND VISUALIZING MALIGNANCY THEREOF

TECHNICAL FIELD

The present invention relates to a method of discriminating longitudinal melanonychia and visualizing malignancy thereof.

BACKGROUND TECHNOLOGY

Nail apparatus melanoma is generally called nail melanoma and appears when a melanocyte present in a nail matrix cancerates. In the case of Japanese, it accounts for about 10% of nail melanomas. Recuperation from the nail apparatus melanoma is considered to be unsatisfactory because making a definite diagnosis of the disease is difficult.

A melanocyte present in a nail matrix is inactive in a normal state and produces no melanin. In some cases, the melanocyte, whether or not it cancerates, starts to produce melanin. As the nail grows, the produced melanin forms a pattern called nail apparatus melanoma. If the melanocyte is not cancerous, the nail apparatus melanoma is considered to be a benign nevus. It is considered that a pattern of the nail apparatus melanoma is usable to determine whether or not the melanocyte present in the nail matrix is cancerous.

However, visually inspecting the pattern with the use of a dermoscope and determining whether the pattern is benign or malignant needs rich experience. In addition, if it is a malignant melanoma, a biopsy is generally not beneficial to the patient. These factors make it difficult to give a definite diagnosis. Such a difficulty is a factor of hindering recuperation. Accordingly, realizing a noninvasive and objective discrimination method of nail apparatus melanoma is strongly needed by clinical sites. Also, a visualization method of visually presenting a difference between benignity and malignity is strongly needed.

To diagnose malignant melanomas except the malignant nail melanoma, various discrimination methods have been proposed based on "randomness" of the shape of an edge of a malignant melanoma. One of the known means to quantify the "randomness" of the shape is a technique of using a pseudo fractal dimension (Patent Document 1). Applying a tumor test, which uses only the pseudo fractal dimension as an index, as it is to discriminating nail apparatus melanoma hardly determines whether a given nail apparatus melanoma is malignant or benign. It is also difficult for the technique to visually present a difference between benignity and malignity.

RELATED ART LITERATURE

Patent Literature

Patent Document 1: Japanese Unexamined Patent Application Publication No. 2008-154761

SUMMARY OF INVENTION

The present invention is able to provide a method that is capable of noninvasively and objectively discriminating between benign and malignant longitudinal melanonychia and visually presenting the malignancy of the longitudinal melanonychia.

Means to Solve Problem

A method of discriminating longitudinal melanonychia according to the present invention is characterized by a first step of assuming a digital color image of longitudinal melanonychia as three-dimensional vectors each composed of RGB parameter values of each pixel and finding a latitudinal variable and a longitudinal variable for each of the three-dimensional vectors in an RGB space, a second step of finding a discrimination index according to a distribution of points defined by the latitudinal and longitudinal variables found in the first step, and a third step of classifying the discrimination index found in the second step according to a threshold and discriminating whether the longitudinal melanonychia is malignant or benign.

A method of visualizing malignancy of longitudinal melanonychia according to the present invention is characterized by displaying the distribution of points of the above-mentioned second step.

MODE OF IMPLEMENTING INVENTION

A preferred embodiment of the present invention will be explained.

Figure 1:
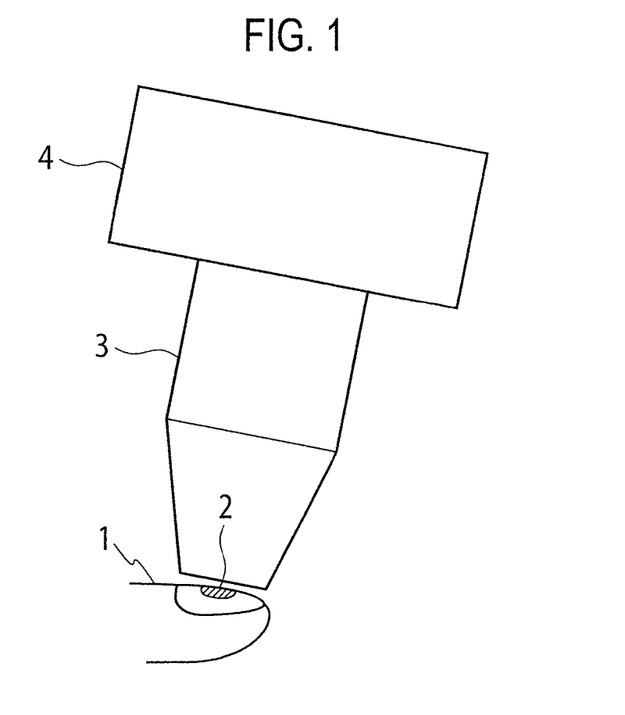
FIG. 1 is a schematic view illustrating an example of an apparatus employed by the present invention

An example of an apparatus employed by the present invention will be explained with reference to FIG. 1. In FIG. 1, 1 is a nail serving as an object. In the nail 1, there is a nail apparatus melanoma 2. The nail apparatus melanoma 2 is photographed with a digital color dermoscope 3. The digital color dermoscope 3 is integral with a CCD camera (two-dimensional solid image pickup apparatus) 4 for taking a color image (JPG format) of the nail apparatus melanoma 2.

From the taken full-scale color image, only a nail is picked up as an analytic object region. From the region, bubbles of jelly used for the photographing and part where diffused reflection is conspicuous are removed.

To effectively use three degrees of freedom possessed by the color image, a three-dimensional vector whose components are RGB parameters is defined in a three-dimensional RGB space. Namely, a three dimensional vector $p_i=(R_i, G_i, B_i)$ whose components are RGB parameter values possessed by each pixel (i-th pixel) in the analytic object region is set.

Figure 2:
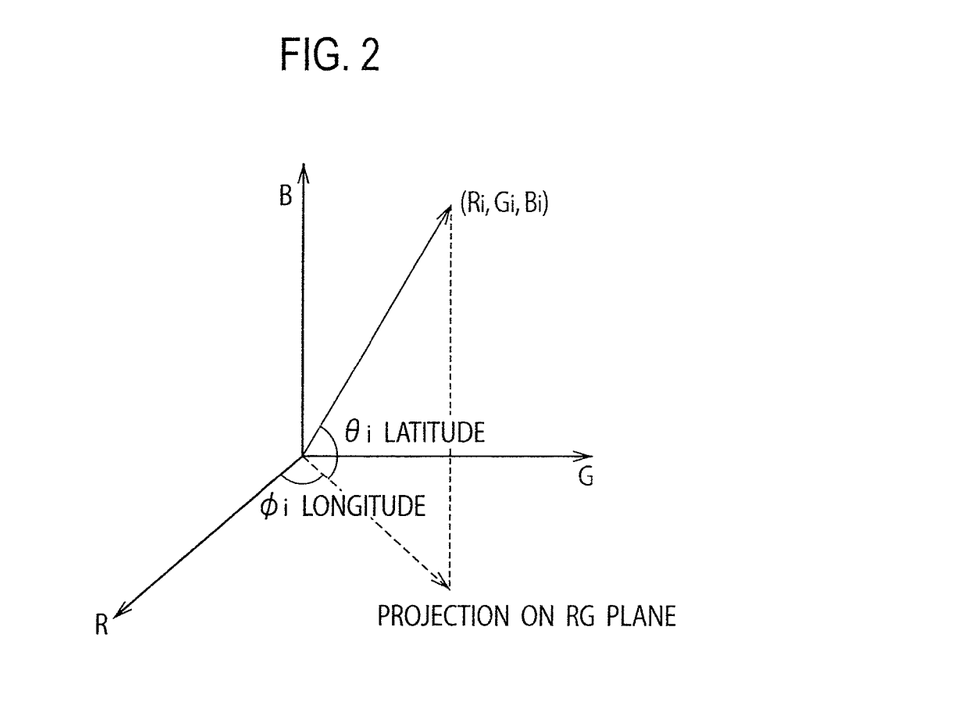
FIG. 2 is coordinates illustrating the definitions of latitudinal and longitudinal variables in a three-dimensional RGB space

Latitudinal and longitudinal variables are obtained in the three-dimensional RGB space (refer to FIG. 2). An RG plane is assumed as an equatorial plane and a latitudinal variable $\theta$ is introduced as an angle between a vector and the RG plane and a longitudinal variable $\phi$ as an angle between a projection of the vector to the RG plane and an R-axis.

The longitudinal variable ($\phi_i$) and latitudinal variable ($\theta_i$) are calculated according to the following mathematical formula 1:

$$\phi_i = \cos^{-1}\left(\frac{R_i}{\sqrt{R_i^2 + G_i^2}}\right), \quad (1)$$

$$\theta_i = \cos^{-1}\left(\frac{\sqrt{R_i^2 + G_i^2}}{\sqrt{R_i^2 + G_i^2 + B_i^2}}\right).$$

A unit of the calculated angle may be of circular measure (rad) or of degree measure (°). In the following explanation, the circular measure (rad) is used for angle measurement.

Angles ($\phi i$, $\theta i$) obtained from the image are plotted on two-dimensional orthogonal coordinates having an abscissa $\phi i$ and an ordinate $\theta i$. A graph thus formed indicates the malignancy of the nail apparatus melanoma.

Instead of forming a distribution of points on the ($\theta$, $\phi$) plane, it is possible to use distances from a point (1, 0, 0) on a unit sphere surface calculated from ($\theta$, $\phi$).

A variance of the plotted points is calculated according to the following mathematical formula 2, to define a discrimination index DI.

$$DI = \sqrt{\frac{1}{N}\sum_{i=1}^{N}\left[(\phi_i - \bar{\phi})^2 + (\theta_i - \bar{\theta})^2\right]} \quad (2)$$

It is possible to define the discrimination index DI by using an average distance from a barycenter of the distribution of the sampled points.

Discrimination indexes for benign and malignant groups are statistically processed, to find an index capable of accurately discriminating the groups from each other and set the index as a threshold. To obtain such a threshold, an ROC (Receiver Operating Characteristics) analysis is used. The ROC analysis is an analytic technique that is based on a graph that plots sensitivities of various thresholds on an ordinate and false positive rates on an abscissa, to evaluate the accuracies of various techniques, compare the techniques with one another, and determine thresholds.

EMBODIMENT

Figure 3:
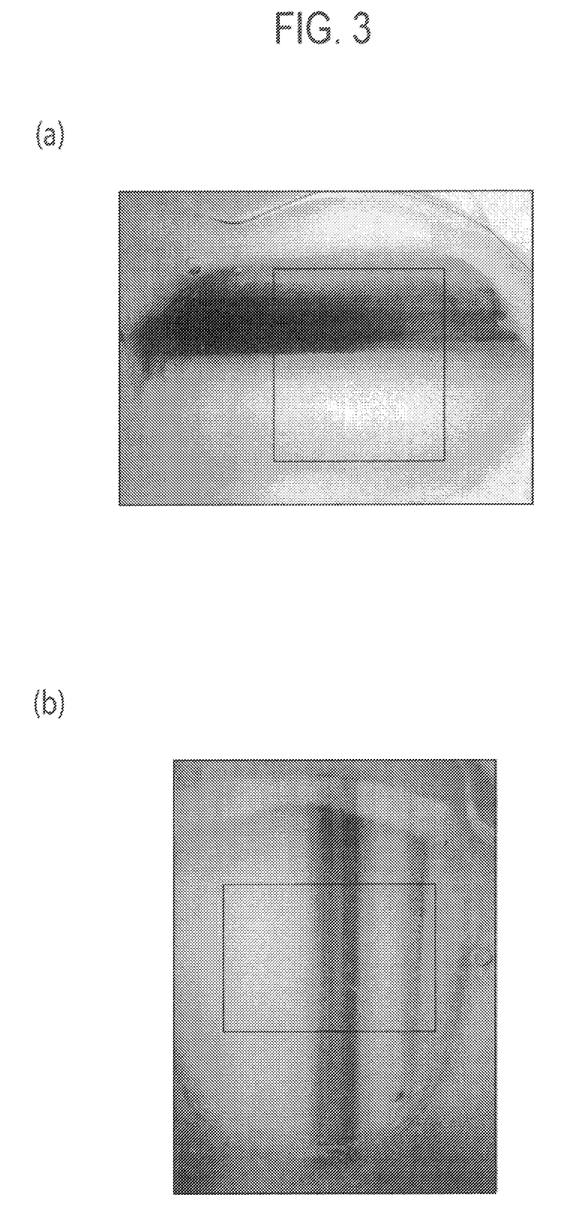
FIG. 3 is digital color dermoscope images illustrating a typical malignant case (a) and a typical benign case (b)

The method of the present invention is applied to six early nail melanoma cases and 25 benign nail nevus cases. FIG. 3 illustrates digital color dermoscope images. FIG. 3(a) is of an early melanoma and FIG. 3(b) is of a benign nevus.

Figure 4:
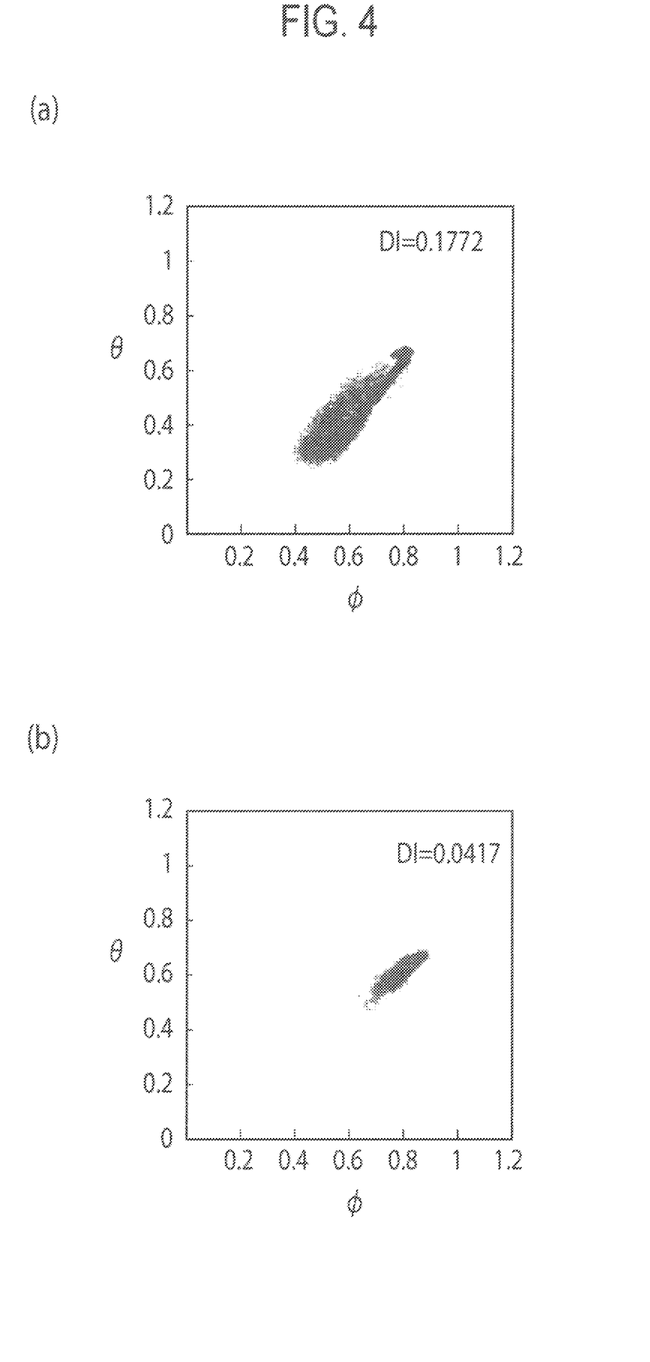
FIG. 4 is distributions of longitudinal and latitudinal variables of a malignant case (a) and benign case (b)

FIG. 4 illustrates distributions of longitudinal and latitudinal variables ($\phi i$, $\theta i$) calculated from the color images. An ordinate represents the latitudinal variable $\theta$ and an abscissa represents the longitudinal variable $\phi$. A circular measure unit system (rad) is used. FIG. 4(a) corresponds to the early melanoma and FIG. 4(b) to the benign nevus. A discrimination index DI of the early melanoma (a) is 0.1772 and that of the benign nevus is 0.0417. As the numeric values indicate, the benign nevus tends to concentrate the variables ($\phi i$, $\theta i$) in a narrow range and the early melanoma tends to spread them. The similar tendencies are observed in the inspected melanoma and nevus groups. This means that the melanoma involves "color diversity". Accordingly, the distributions of the variables ($\phi i$, $\theta i$) illustrated in FIG. 4 are usable to subjectively understand that a narrow distribution is a nevus and a wide distribution is a nail apparatus melanoma. This expression easily appeals to the eyes of a viewer. The objectivity of this expression will improve if the discrimination index DI is added thereto as illustrated in FIG. 4. This is because a p-value of the DI values of the melanoma and nevus groups is p<1.0×10$^{-5}$. Here, the p-value is a probability of accidentally causing a difference between the DI values of the melanoma group and those of the nevus group. The smaller the p-value, the more the significance of the DI value difference between the groups improves.

Figure 5:
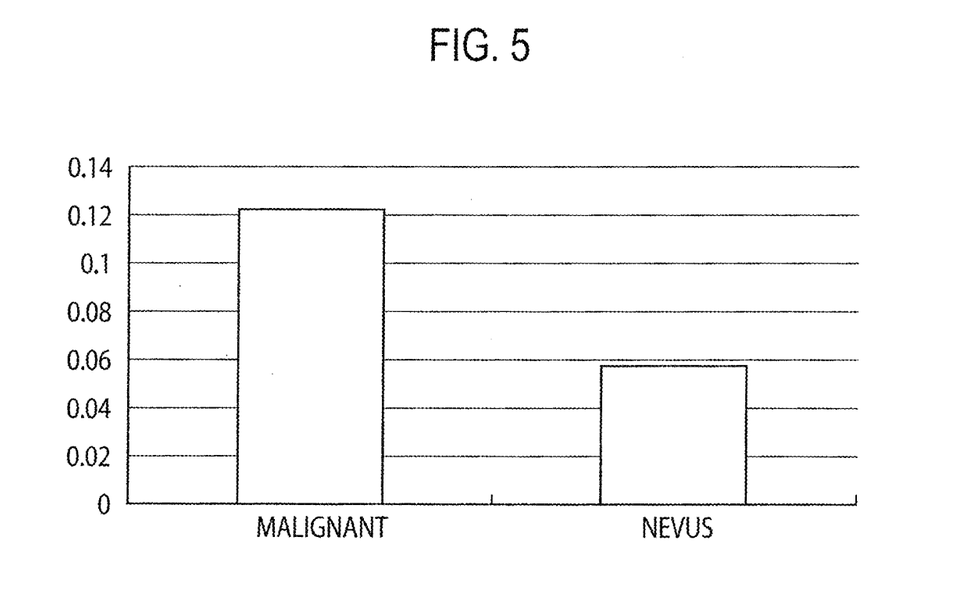
FIG. 5 is a graph illustrating average values of discrimination indexes of malignant and benign groups

Table 1 lists the DI values of the 31 cases. FIG. 5 illustrates a result of Student's t-test.

| Early melanoma | | Nevus | | | |
|---|---|---|---|---|---|
| No. | DI | No. | DI | No. | DI |
| 1 | 0.1299 | 7 | 0.0639 | 20 | 0.0263 |
| 2 | 0.1772 | 8 | 0.0293 | 21 | 0.0463 |
| 3 | 0.1376 | 9 | 0.0561 | 22 | 0.0171 |
| 4 | 0.092 | 10 | 0.045 | 23 | 0.0579 |
| 5 | 0.1026 | 11 | 0.0675 | 24 | 0.075 |
| 6 | 0.092 | 12 | 0.065 | 25 | 0.0778 |
| | | 13 | 0.0407 | 26 | 0.0489 |
| | | 14 | 0.0573 | 27 | 0.0481 |
| | | 15 | 0.0417 | 28 | 0.0366 |
| | | 16 | 0.0727 | 29 | 0.0905 |
| | | 17 | 0.037 | 30 | 0.0695 |
| | | 18 | 0.0337 | 31 | 0.1268 |
| | | 19 | 0.0988 | | |

Figure 6:
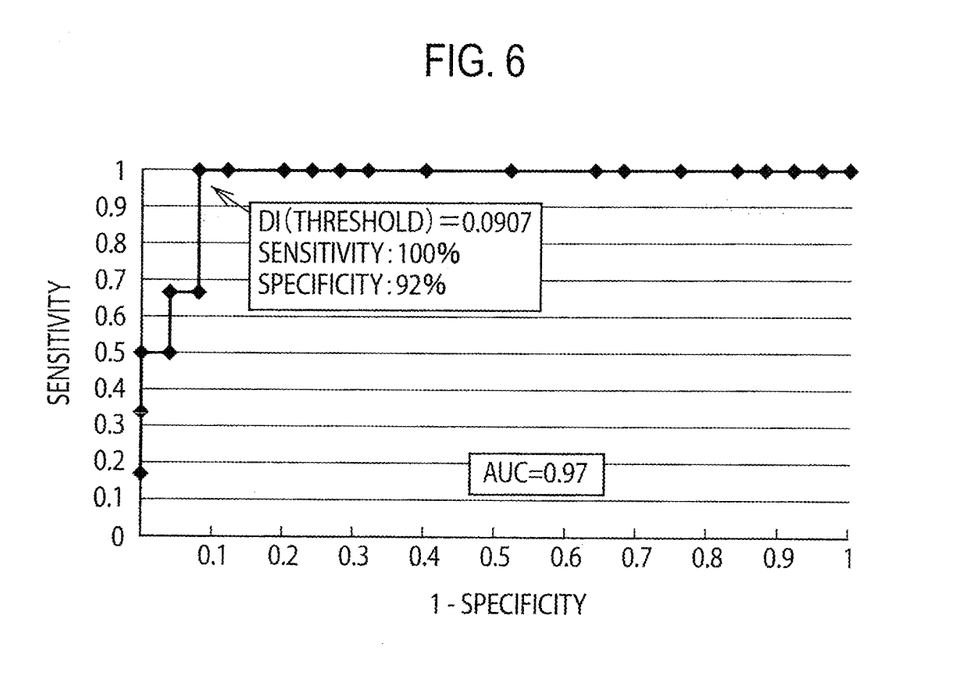
FIG. 6 is a graph illustrating an ROC analysis result of discrimination indexes

FIG. 6 illustrates an examination result of an early melanoma discrimination performance according to a variance of a distribution of latitudinal and longitudinal variables ($\phi i$, $\theta i$). This is a so-called ROC curve. In FIG. 6, an ordinate represents a sensitivity (a probability of correctly diagnosing an early melanoma) and an abscissa represents a false positive rate(=1−specificity) that is a probability of misdiagnosing a nevus as a melanoma. The specificity is a probability of correctly diagnosing a nevus. A point (0, 1) is defined as a point to give a 100% correct diagnosis. Generally, the graph of FIG. 6 is usable for evaluating performance in three ways.

1) Performance is indicated with the sensitivity and specificity of a point that is closest to (0, 1) on the curve.

2) Performance is compared according to a maximum product of sensitivity and specificity at a point on the ROC curve.

3) Performance is evaluated according to an area AUC (Area Under Curve) surrounded by the curve.

In FIG. 6, a discrimination index DI based on latitudinal and longitudinal variables ($\phi i$, $\theta i$) provides the same point for 1) and 2) and a discrimination index DI of 0.0907 provides a sensitivity of 100% and a specificity of 92%. This DI value may be considered as a threshold to discriminate an early melanoma from a nevus. A DI value greater than the threshold is determined to be an early melanoma and that smaller than the threshold is determined to be a nevus. In FIG. 6, performance based on 3) is AUC=0.97. In this way, adding a discrimination index DI to a graph of a diagnosing part contributes to an easy visual understanding and secures objectivity.

The mechanical diagnostic results with the discrimination indexes DI are compared with diagnostic results by medical specialists. The former diagnostic results almost match the latter diagnostic results.

Figure 7:
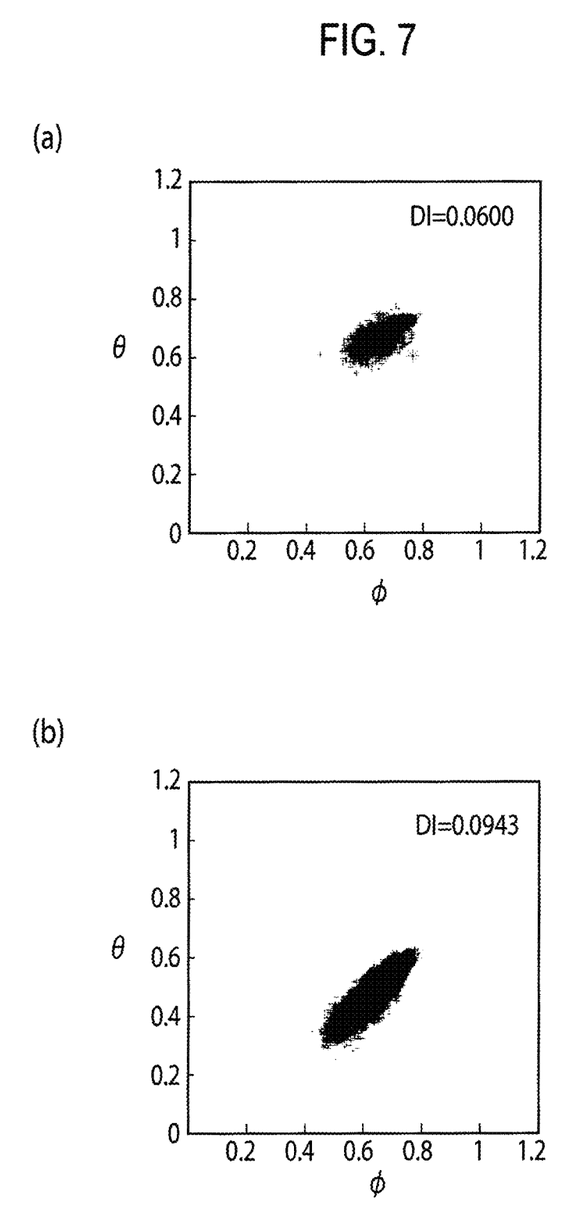
FIG. 7 is distributions of longitudinal and latitudinal variables of a follow-up case

FIG. 7 illustrates an interesting case not included in the above-mentioned statistically processed cases. This case is excluded from the statistically processed cases because it is presently under follow-up. The case has been put in follow-up care at a first dermoscope photographing, and 1.5 months later, has again been photographed and subjected to a biopsy. In terms of histopathology, the case is difficult to discriminate between a melanoma and a nevus. Illustrated in FIG. 7 are temporal changes in a distribution of longitudinal and latitudinal variables (φi, θi) and discrimination index DI. The method of the present invention determines from a first dermoscope image of FIG. 7(a) and a DI value at the time that the case is a nevus, and from a second image of FIG. 7(b) taken 1.5 months later and a DI value at the time, that the case is an early melanoma. It is understood that the changes in the distribution of longitudinal and latitudinal variables (φi, θi) are linked to the changes in the discrimination index DI. This case suggests that the method of the present invention is effective not only when determining whether or not a given case is a melanoma but also during follow-up care or when discriminating whether or not a given case needs follow-up care.

EFFECTS OF INVENTION

The longitudinal melanonychia discrimination method according to the present invention effectively uses three degrees of freedom originally possessed by a color image as three-dimensional vectors without depending on specific reference vectors, to noninvasively and objectively discriminate longitudinal melanonychia.

The longitudinal melanonychia malignancy visualization method according to the present invention allows the degree of malignancy to be visually confiutted as a distribution of points instead of numerical values and realizes an easy understanding of discrimination condition.

(United States Designation)

In connection with United States designation, this international patent application claims the benefit of priority under 35 U.S.C. 119(a) to Japanese Patent Application No. 2009-292289 filed on Dec. 24, 2009, the entire content of which is incorporated by reference herein.

The invention claimed is:

1. A method of discriminating longitudinal melanonychia, comprising:
   representing, by a processor, a digital color image of nail apparatus melanoma as three-dimensional vectors, each composed of RGB parameter values of each imaged pixel,
   calculating, by a processor, a latitudinal variable $\theta_i$ and a longitudinal variable $\phi_i$ for each of the three-dimensional vectors in an RGB space, based on the following equations:

$$\phi_i = \cos^{-1}\left(\frac{R_i}{\sqrt{R_i^2 + G_i^2}}\right),$$

and $$\theta_i = \cos^{-1}\left(\frac{\sqrt{R_i^2 + G_i^2}}{\sqrt{R_i^2 + G_i^2 + B_i^2}}\right),$$

where $R_i$, $G_i$, and $B_i$ indicate the RGB parameter values of a three-dimensional vector of pixel i;
   calculating, by a processor, a discrimination index according to a distribution of points defined by the latitudinal and longitudinal variables; and
   classifying, by a processor, the found discrimination index according to a threshold and discriminating whether the nail apparatus melanoma is malignant or benign,
   wherein the discrimination index DI is calculated according to the distribution of the points defined by the latitudinal and longitudinal variables, based on the following equation:

$$DI = \sqrt{\frac{1}{N}\sum_{i=1}^{N}\left[(\phi_i - \bar{\phi})^2 + (\theta_i - \bar{\theta})^2\right]},$$

where N indicates a total number of points; $\bar{\phi}$ indicates an average value of the longitudinal variables of N points; and $\bar{\theta}$ indicates an average value of the latitudinal variables of N points, and
   wherein, when the discrimination index is smaller than the threshold, the nail apparatus melanoma is classified as benign, and when the discrimination index is greater than the threshold, the nail apparatus melanoma is classified as malignant.

2. The method according to claim 1, further comprising displaying the distribution of the points.

* * * * *

UNITED STATES PATENT AND TRADEMARK OFFICE
CERTIFICATE OF CORRECTION

PATENT NO. : 9,049,991 B2
APPLICATION NO. : 13/518589
DATED : June 9, 2015
INVENTOR(S) : T. Sota et al.

It is certified that error appears in the above-identified patent and that said Letters Patent is hereby corrected as shown below:

On the Title Page, (73) Assignee, please change "Kohko" to --Kohki--.

Signed and Sealed this
Eighth Day of December, 2015

Michelle K. Lee
*Director of the United States Patent and Trademark Office*